United States Patent [19]

Grego

[11] Patent Number: 4,762,414
[45] Date of Patent: Aug. 9, 1988

[54] STATIC INTERFEROMETRIC ELLIPSOMETER

[75] Inventor: Giorgio Grego, Venaria, Italy

[73] Assignee: Cselt-Centro Studi e Laboratori Telecomunicazioni S.P.A., Turin, Italy

[21] Appl. No.: 850,493

[22] Filed: Apr. 10, 1986

[30] Foreign Application Priority Data

Apr. 23, 1985 [IT] Italy ................ 67378 A/85

[51] Int. Cl.[4] ............................................. G01B 9/02
[52] U.S. Cl. .................................. 356/349; 356/351; 356/357
[58] Field of Search ................ 356/349, 351, 357, 369

[56] References Cited

U.S. PATENT DOCUMENTS 4,053,232 10/1977 Dill et al.
4,553,841 11/1985 Coppa et al. ........................ 356/349

FOREIGN PATENT DOCUMENTS 0075689 4/1983 European Pat. Off.
0165722 12/1985 Japan ................................. 356/369

OTHER PUBLICATIONS

Levites et al., "A Heterodyne Laser Interferometer with an Acousto-Optical Modulator", Moscow Machine-Toll Institute, Nov.-Dec. 1973, No. 6, pp. 139–140.
Analysis of Thin Films by Interferometric Ellipsometry by H. F. Hazebroek, A. A. Holscher, Japanese Journal of Applied Physics, suppl. 2, pt. 1, pp. 673–676, 1974, Japanese Journal of Applied Physics, Tokyo 105, Japan Interference Ellipsometer by D. P. Pilipko and I. P. Pugach, 8164 Instruments and Experimental Techniques, pp. 951–952, 26 (1983), Jul.-Aug., No. 4, Part 2, New York, NY.
R. M. A. Azzam and N. M. Bashara, article "Interferometric Ellipsometers"—Ellipsometry and Polarized LIght—North-Holland Publishing Co.—1977
F. Hazebroek and W. M. Visser, "Automated Laser Interferometric Ellipsometry and Precision Reflectometry"—1983—Journal of Physics.

Primary Examiner—Davis L. Willis
Assistant Examiner—Matthew W. Koren
Attorney, Agent, or Firm—Karl F. Ross; Herbert Dubno

[57] ABSTRACT

A static interferometric ellipsometer, wherein a source (3) generates a coherent light-beam with two monochromatic radiations at slightly different frequencies. A first photodetector (6) generates a first beat between the two radiations, to be used as reference. A second photodetector (9) generates a second beat between the two radiations, after they have been polarized in perpendicular planes and separated so that one of them is reflected onto the photodetector (9) by the sample under test (1,2). A measuring and computing system (11) determines the optical properties of said sample starting from the intensity of the second beat and from the relative phase between the two beats.

3 Claims, 1 Drawing Sheet

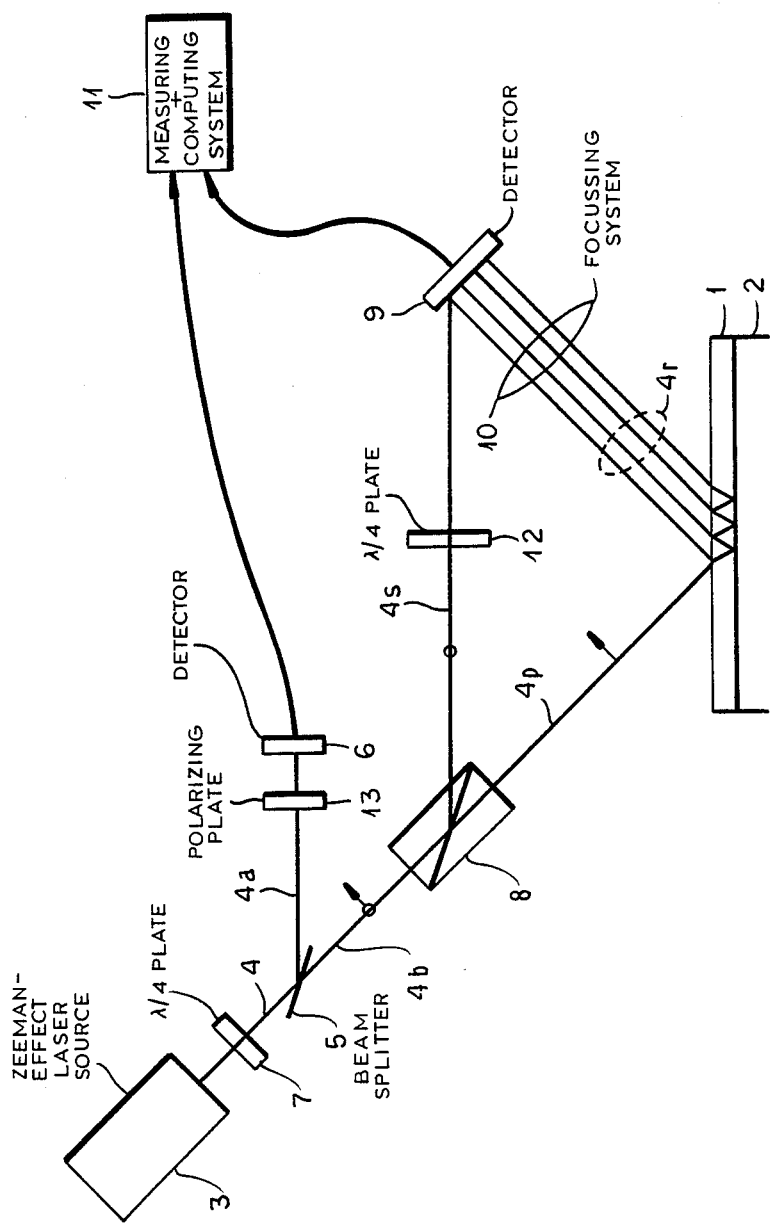

STATIC INTERFEROMETRIC ELLIPSOMETER

FIELD OF THE INVENTION

The present invention refers to devices for measuring optical properties of bodies and more particularly concerns an interferometric ellipsometer.

BACKGROUND OF THE INVENTION

Ellipsometry is a measurement technique allowing the study of properties of reflecting bodies from the knowledge of the reflection effects on the state of polarization of a light beam. Ellipsometry exploits the fact that, upon directing polarized light onto a surface there is a variation in the relative phase between a component polarized in the incidence plane and the component polarized in the perpendicular plane, and a variation in the ratio between the amplitudes of the two components. By indicating by $\beta_{pi}, \beta_{si}, \beta_{pr}, \beta_{sr}$ the phases of the components of the incident and the reflected beam polarized in the incidence plane and in the perpendicular plane, respectively, and by Ep, Es, Rp, Rs the amplitudes of the components of the incident and reflected beam, an ellipsometer allows measurement of angles:

$$\Delta = (\beta_{pr} - \beta_{sr}) - (\beta_{pi} - \beta_{si})$$

$$\psi = \arctan \frac{Rp}{Rs} \cdot \frac{Es}{Ep}$$

The values of $\Delta, \psi$ depend according to known relations on the properties of the body under test, more particularly on the thickness and the refractive index. Considering a body mounted on a substrate and assuming that Es=Ep, the following relation applies:

$$\tan \psi \, e^{i\Delta} = \frac{R_p}{R_s} \cdot e^{i\Delta} = \qquad (1)$$

$$\frac{(r_{01})_p + (r_{12})_p \, e^{-2i\delta}}{1 + (r_{01})_p (r_{12})_p \, e^{-2i\delta}} \cdot \frac{(r_{01})_s + (r_{12})_s \, e^{-2i\delta}}{1 + (r_{01})_s (r_{12})_s \, e^{-2i\delta}}$$

where $r_{01}$ is the reflection coefficient at the separation surface between the medium (e.g. air) in which the test body is immersed and the body itself; $r_{12}$ is the reflection coefficient at the separation surface between the body and the substrate; subscripts p,s indicate that the reflection coefficient is relevant to the wave polarized in the incidence plane or in the perpendicular plane; $\delta = (360/\lambda) \cdot d(n_1^2 - \sin^2\phi)^{\frac{1}{2}}$ is the phase shift undergone by rays reflected by the substrate at each crossing of the body with thickness d and refractive index $n_1$ with respect to the rays reflected by the surface of the body, $\phi$ being the incidence angle of the beam on the body.

Relationship (1) takes into account multiple reflections on the separation surface between the body and air and between the substrate and the body.

Reflection coefficients $r_{01}, r_{12}$ are tied to the refractive indices of the different media by the well-known Fresnel formulae which are given here for $r_{01}$:

$$(r_{01})_p = \frac{n_1 \cos \phi_1 - n_0 \cos \phi}{n_1 \cos \phi_1 + n_0 \cos \phi} \qquad (2)$$

$$(r_{01})_s = \frac{n_0 \cos \phi_1 - n_1 \cos \phi}{n_0 \cos \phi_1 + n_1 \cos \phi}$$

where $\phi_1$ is the refraction angle of rays with incidence angle $\phi$.

Many commercially available ellipsometers are based on the extinction principle: the light emitted by a source and polarized in a polarizer traverses a compensator which is adjusted so as to introduce equal and opposite phase-shifts to those caused by reflection, thereby originating a linearly-polarized radiation; the latter, after reflection, is collected by an analyser which is in turn adjusted so as to cause the extinction.

The magnitude of the compensator adjustment gives $\Delta$ and that of the analyzer adjustment gives $\psi$. It is clear that the measurement by these devices is very slow, since the compensator and analyzer adjustments interact with each other.

These disadvantages are overcome by ellipsometers based on interferometric techniques. An ellipsometer of this kind is described in "Ellipsometry and polarized light" by R. M. Azzam and N. M. Bashara, North-Holland Publishing Company, 1977, pages 262 to 265, and in the article "Automated laser interferometric ellipsometry and precision reflectometry" by H. F. Hazebroek e W. M. Wisser, Journal of Physics, Section E, Vol. 16, 1983.

In such an ellipsometer a polarized beam of radiation is divided by a beam-splitter into two beams. One beam is sent towards the sample under test and is reflected on a mirror by which it is retroreflected towards the sample and the splitter; the other, acting as reference beam, is sent to a corner reflector, reflected onto a mirror and sent back from here to the reflector and the splitter. The two beams are recombined by the splitter into a single beam whose components parallel and perpendicular to the plane of incidence on the sample are separated and sent to different detectors. The corner reflector is translated at a constant speed so as to cause a frequency variation in the reference beam by Doppler effect.

This interferometric ellipsometer has a number of disadvantages. More particularly, the corner reflector position is critical, as it has to be chosen so as to make incident reference radiation coincide with one of the two reflector self-polarizations, to maintain the reference radiation polarization. The position of the mirror in the measurement branch is critical too, since the mirror must be accurately perpendicular to the light reflected by the sample to prevent polarization variations and to make the two reflections take place on the sample at the same point. Besides, the ellipsometer includes moving parts which always entail reliability problems.

SUMMARY OF THE INVENTION

The present invention provides an ellipsometer wherein neither components with critical positions nor moving parts are provided.

The invention provides an interferometric ellipsometer for measuring the optical properties of a sample of reflecting material, comprising means generating a polarized light beam to be sent to the sample and means collecting the beam reflected by the sample. According to the invention the means generating the beam to be sent to the sample generates a beam comprising two monochromatic light radiations with slightly different frequencies, and is associated with means for extracting a fraction of the beam comprising the two radiations and sending this fraction to a first photodetector generating a first beat between the two radiations.

Means is provided to linearly polarize the two radiations in two perpendicular planes, and the ellipsometer includes means separating the radiations at the two frequencies and sending one of them to a second detector and the other towards the sample. The second photodetector is arranged so as to receive also the radiation forming the beam reflected from the surface of the sample which reflected beam presents such a polarization plane as to comprise a component polarized in the same plane as said one radiation, and generates a second beat between the radiations at the two frequencies, which second beat has an amplitude proportional to the amplitude of the said component of the reflected beam and a phase, relative to the first beat, depending on the phases shift between said component of the reflected beam and the radiation directly sent to the second detector.

The ellipsometer is also characterized by a measuring and computing system deriving the values of the optical properties of the test sample from the amplitude and phase values of the second beat.

The beam generating means can include a Zeeman-effect laser associated with a quarter lambda plate placed downstream thereof, a beam splitter followed by a polarization separating device separating the two radiations.

The beam generating means can comprise a monomode laser followed by an acousto-optical device emitting the two radiations according to two different paths along which the means linearly polarizing the two radiations in perpendicular planes are arranged.

One of the perpendicular planes can coincide with the plane of incidence on the sample and the polarization separating means can send the radiation polarized in the incidence plane towards the sample.

The radiation sent towards the sample can be sent as a diverging beam.

BRIEF DESCRIPTION OF THE DRAWING

The sole FIGURE of the accompanying drawing shows the ellipsometer according to the invention in schematic form.

SPECIFIC DESCRIPTION

The drawing shows the use of the ellipsometer to measure the refractive index and the thickness of a thin opaque layer 1 carried by a substrate 2. The means supporting the various components of the ellipsometer and the test sample are not shown, because they are analogous to those of conventional ellipsometers. Thick lines denote electrical connections, and thin lines light paths.

The ellipsometer comprises a source 3 which generates a beam 4 comprising radiations at two frequencies $f_1$, $f_2$, which are slightly different from each other (with a difference of the order of some MHz). The source can be a Zeeman-effect laser which generates the two frequencies, or a monomode laser associated with an acousto-optical cell emitting the laser-generated frequency and a second frequency, equal either to the sum or to the difference between the laser-generated frequency and the cell-driving radiofrequency.

The drawing shows a Zeeman-effect laser which generates two radiations circularly polarized in opposite directions. Beam 4 emitted from the source is sent to a λ/4 plate 7 converting the two circularly-polarized radiations into two radiations linearly polarized in orthogonal planes, which for sake of simplicity are assumed to coincide with the plane of incidence on the sample and with the perpendicular plane. This assumption does not entail loss of generality, as the above arrangement may be obtained by suitably mounting the ellipsometer components and/or the sample. Plate 7 is followed by a beam splitter 5 splitting the beam into two fractions 4a, 4b. One fraction 4a is sent through a polarizing plate 13 with axis inclined by 45° to the two components of beam 4 to a first detector 6 generating an electric signal representing the beat between the two frequencies. The second fraction 4b is sent to a device 8 for separating the polarization (e.g. a Nichol or Wollaston or Glan-Taylor prism) which sends radiation 4s polarized in the plane perpendicular to the incidence plane to a second photodiode 9 through another λ/4 plate 12. The other radiation, 4p, is sent towards layer 1 and is reflected by it and by substrate 2. If necessary, an optical system 10 focuses the reflected beam 4r onto photodiode 9.

Due to multiple reflections at the interface between air and layer 1 and between layer 1 and substrate 2, the amplitude and the time phase of radiation 4p will change, while the polarization plane remains the same. Detector 9 creates therefore a second low frequency beat between reflected beam 4r and beam 4s rotated by 90° by plate 12.

By taking into account that radiation 4s has undergone no alteration, the amplitude of this second beat depends on the amplitude of beam 4r and is given by $Ap = k \cdot Rp$, k being a constant depending on the gain of the electronic circuitry. Since radiations 4s, 4p have the same starting phase as beam 4a, the relative phase between the beat generated by photodetector 9 and that generated by photodetector 6 represents phase shift $\Delta$ generated by the reflection.

A measuring and computing system 11, connected to the two photodetectors 6, 9, measures the phase and amplitude values of the beats thus generated and obtains the values of refractive index $n_1$ and thickness d by applying relations (1) and (2).

By substituting the expression for $\delta$, formulae (2) and the corresponding ones for $r_{12}$ (where $n_o$ is known) in relation (1), by applying Snell law so as to have only angle $\phi$, and by separating the real part of (1) from the imaginary one, two equations are obtained which relate respectively $\Delta$ and $\psi$ to $n_1$ and d and can be solved by the computing system 11.

It is to be appreciated that only component 4p is reflected by the sample, so that the 3rd member in relation (1) is reduced to the 1st factor, which corresponds to $Rp\, e^{i\delta}p$.

The measure carried out by using only one component of beam 4 would already supply the values requested. Yet, in order to eliminate possible effects due to optical path outside the sample, which path is different for the two components of beam 4, measuring and computing system 11 can store the values of Ap and $\delta_p$ and the measure can be repeated by sending to layer 1 component 4s, thereby to obtain As and $\delta_s$.

From the knowledge of Ap, As, $\delta_p$, $\delta_s$, taking into account that $$\tan \psi \, e^{i\Delta} = \frac{Ap}{A_s} e^{i(\delta p - \delta s)}$$

relation (1) can be applied in its complete form and a measure not affected by the differences of optical path outside the sample is obtained.

It is to be noted that, unlike component 4p, component 4s undergoes because of the reflections a rotation of its plane of polarization, so that only a component of the reflected beam interferes with component 4p. The same holds if the polarization planes of the two radiations of beam 4 do not coincide with the incidence plane on the sample and with the perpendicular one.

Obviously, the measurement thus effected concerns a limited area of the surface of layer 1; to have the complete information it is sufficient to translate the sample on the support or to change the source orientation and to repeat the measures. As an alternative, to reduce or eliminate the need for such displacements, a diverging beam could be sent towards the sample; thus, also possible dependence on the launching angle is compensated.

It is clear that what described has been given only by way of non limiting example and that variations and modifications are possible without going out of the scope of the invention.

More particularly, in case the two frequencies are generated by a monomode laser and by an acousto-optical cell, the two frequencies are emitted according to different paths and a suitable optical system will be necessary to combine them on photodiode 6; besides, separated polarizers will be necessary instead of a single λ/4 plate 7.

Moreover, in the case of measurement with a single beam component, radiations sent on the sample and on photodiode 9 can be mutually exchanged: however, the solution described provides more information on the optical properties of the sample since it allows the Brewster angle to be determined. In fact in correspondence with that angle, beam 4d is completely reflected by the external surface of layer 1 and beam 4e then consists only of the beams reflected by the surface separating layer 1 and support 2: by varying the incidence angle, in correspondence with Brewster angle a discontinuity will be present in the beat amplitude.

I claim:

1. An interferometric ellipsometer for measuring optical properties of a sample, comprising:
   a light source generating a beam of two monochromatic light radiations with slightly different frequencies;
   polarizing means in the path of said beam for linearly polarizing the two monochromatic light radiations thereof in two perpendicular planes;
   a beam splitter in the path of the beam generated by said light source for subdividing said beam into a first fractional beam and a second fractional beam each composed of said two monochromatic light radiations with slightly different frequencies and for directing said fractional beams along separate paths;
   a first photodetector in the path of said first fractional beam receiving said first fractional beam without passage through and reflection by said sample for generating a first beat from said two monochromatic light radiations;
   separating means in the path of said second fractional beam for separating the second fractional beam into two light beams of different polarization planes and transmitting the two light beams of different polarization planes respectively along first and second noncoincident paths;
   a second photodetector disposed along said first path and receiving the light beam of one of said polarization planes transmitted therealong without passing through said sample;
   means for positioning said sample in said second path, for collecting radiation reflected from said sample into a reflected beam having a component polarized in the same plane as said light beam transmitted along said first path, and directing said reflected beam onto said second photodetector to generate a second beat frequency between said two monochromatic light radiations with slightly different frequencies whereby said second beat has an amplitude proportional to the magnitude of said component and a phase relative to the first beat depending upon the phase shift between said component of said reflected beam and said light beam transmitted along said first path; and
   measuring and computing means electrically connected to said first and second detectors for calculating values of said optical properties from said amplitude and the phase of said second beat relative to said first beat.

2. The ellipsometer defined in claim 1 wherein said light source is a Zeeman-effect laser, and said polarizing means is a quarter-lamda plate, in the path of said beam ahead of said beam splitter.

3. The ellipsometer defined in claim 1 wherein one of the perpendicular planes coincides with the plane of incidence of said light beam transmitted along said second path upon said sample and said separating means transmits the radiation polarized in said plane of incidence along second path.

* * * * *